(12) United States Patent
McManus

(10) Patent No.: US 10,631,908 B2
(45) Date of Patent: Apr. 28, 2020

(54) INTRAMEDULLARY NAIL INSERTION HANDLE

(71) Applicant: DePuy Synthes Products, Inc., Raynham, MA (US)

(72) Inventor: Joshua McManus, West Chester, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 83 days.

(21) Appl. No.: 15/613,639

(22) Filed: Jun. 5, 2017

(65) Prior Publication Data
US 2018/0344377 A1  Dec. 6, 2018

(51) Int. Cl.
| A61B 17/92 | (2006.01) |
| A61B 17/72 | (2006.01) |
| A61B 17/88 | (2006.01) |
| A61B 90/00 | (2016.01) |
| A61B 17/00 | (2006.01) |

(52) U.S. Cl.
CPC ............ *A61B 17/921* (2013.01); *A61B 17/72* (2013.01); *A61B 17/8872* (2013.01); *A61B 2017/00469* (2013.01); *A61B 2090/034* (2016.02)

(58) Field of Classification Search
CPC .............................. A61B 17/72; A61B 17/921
See application file for complete search history.

(56) References Cited

U.S. PATENT DOCUMENTS

| 5,480,402 A | 1/1996 | Kim |
| 5,766,174 A | 6/1998 | Perry |
| 6,692,530 B2 * | 2/2004 | Doubler ............... A61F 2/36 606/62 |
| 7,033,365 B2 | 4/2006 | Powell et al. |
| 2008/0281331 A1 | 11/2008 | Fritzinger et al. |
| 2011/0009865 A1 | 1/2011 | Orfaly |
| 2013/0041414 A1 | 2/2013 | Epperly et al. |
| 2015/0148849 A1 | 5/2015 | Abidin |

FOREIGN PATENT DOCUMENTS

| EP | 1759643 A1 | 3/2007 |
| WO | 98/32387 A1 | 7/1998 |

OTHER PUBLICATIONS

European Search Report (EP 18175775.8) dated Mar. 22, 2019, 11 pages.

* cited by examiner

Primary Examiner — Christian A Sevilla
(74) Attorney, Agent, or Firm — Wayne C. Jaeschke, Jr.

(57) ABSTRACT

In one embodiment, an intramedullary nail insertion system has a handle, a coupler, and a securement member. The handle has a body that includes a distal body end, and a proximal body end that is spaced from the distal body end along a proximal direction. Further, the handle defines an aperture that extends from the distal body end to the proximal body end. The coupler includes a distal coupler end having a first fastener that fastens to an intramedullary nail, and includes a proximal coupler end having a second fastener sized to be received through the distal body end in the proximal direction into the aperture of the handle. The securement member has a third fastener that fastens to the second fastener of the coupler so as to capture the handle body between the securement member and the intramedullary nail. The system can be assembled using a two-handed operation.

18 Claims, 7 Drawing Sheets

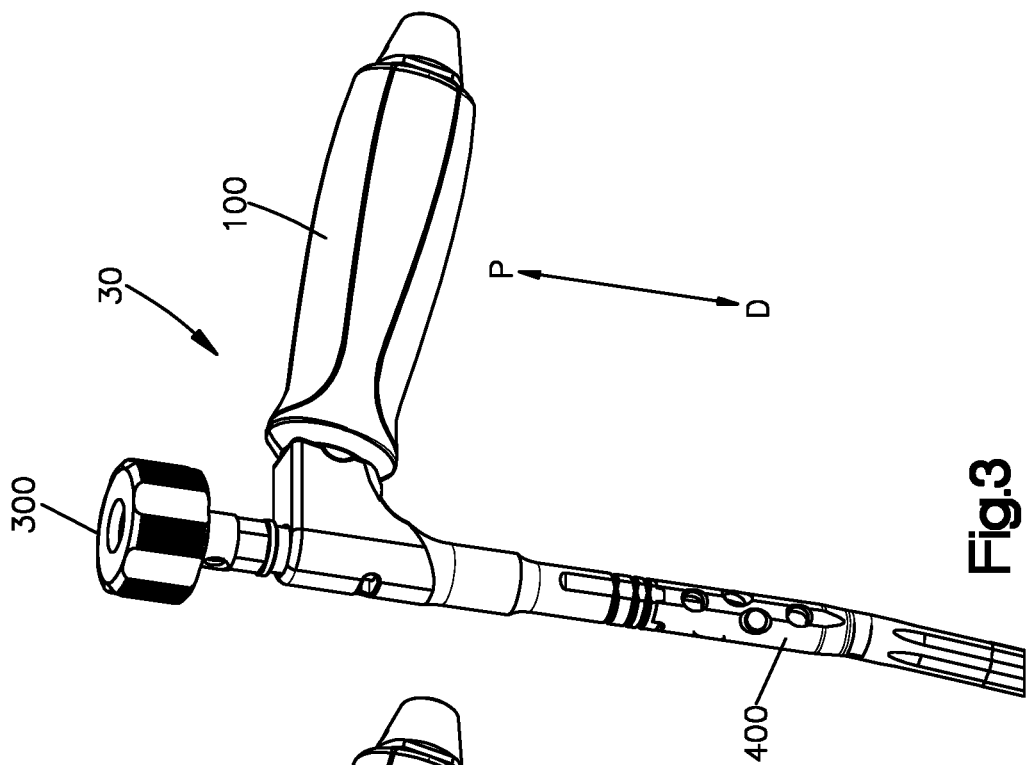
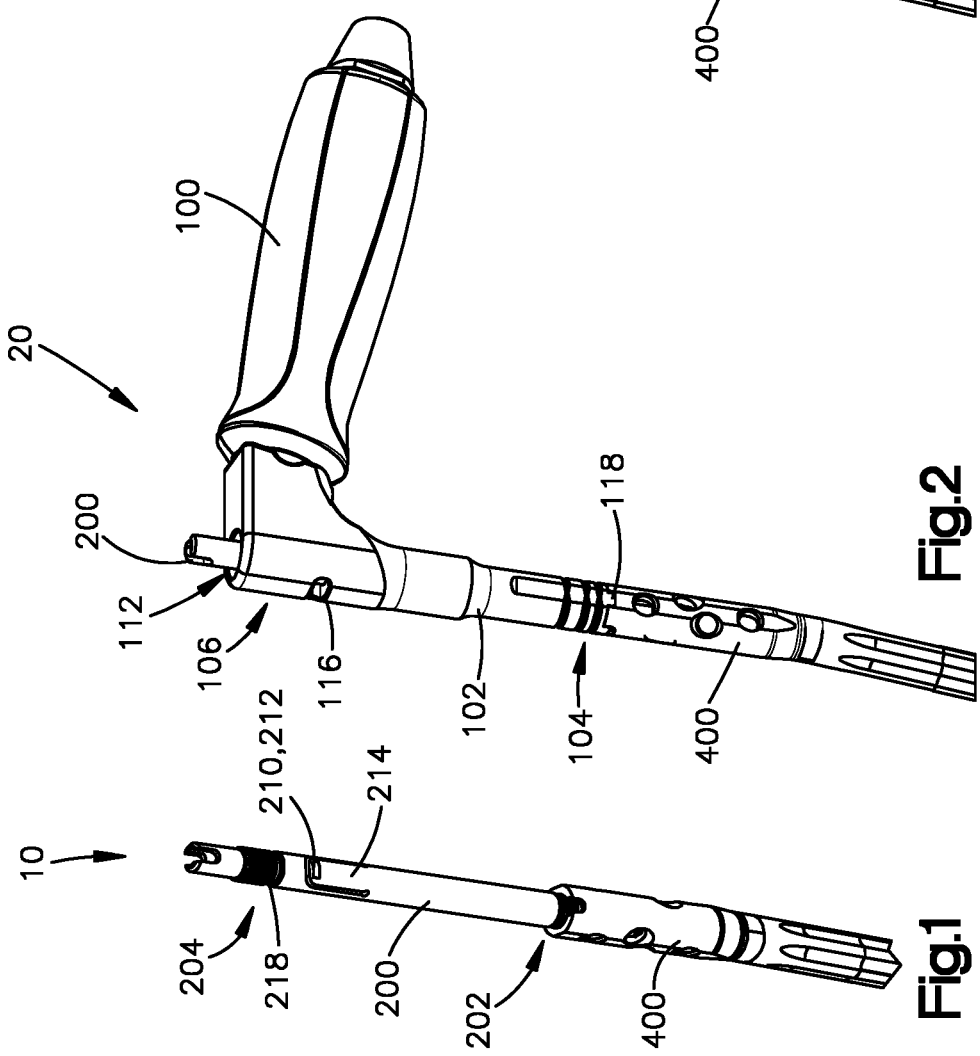

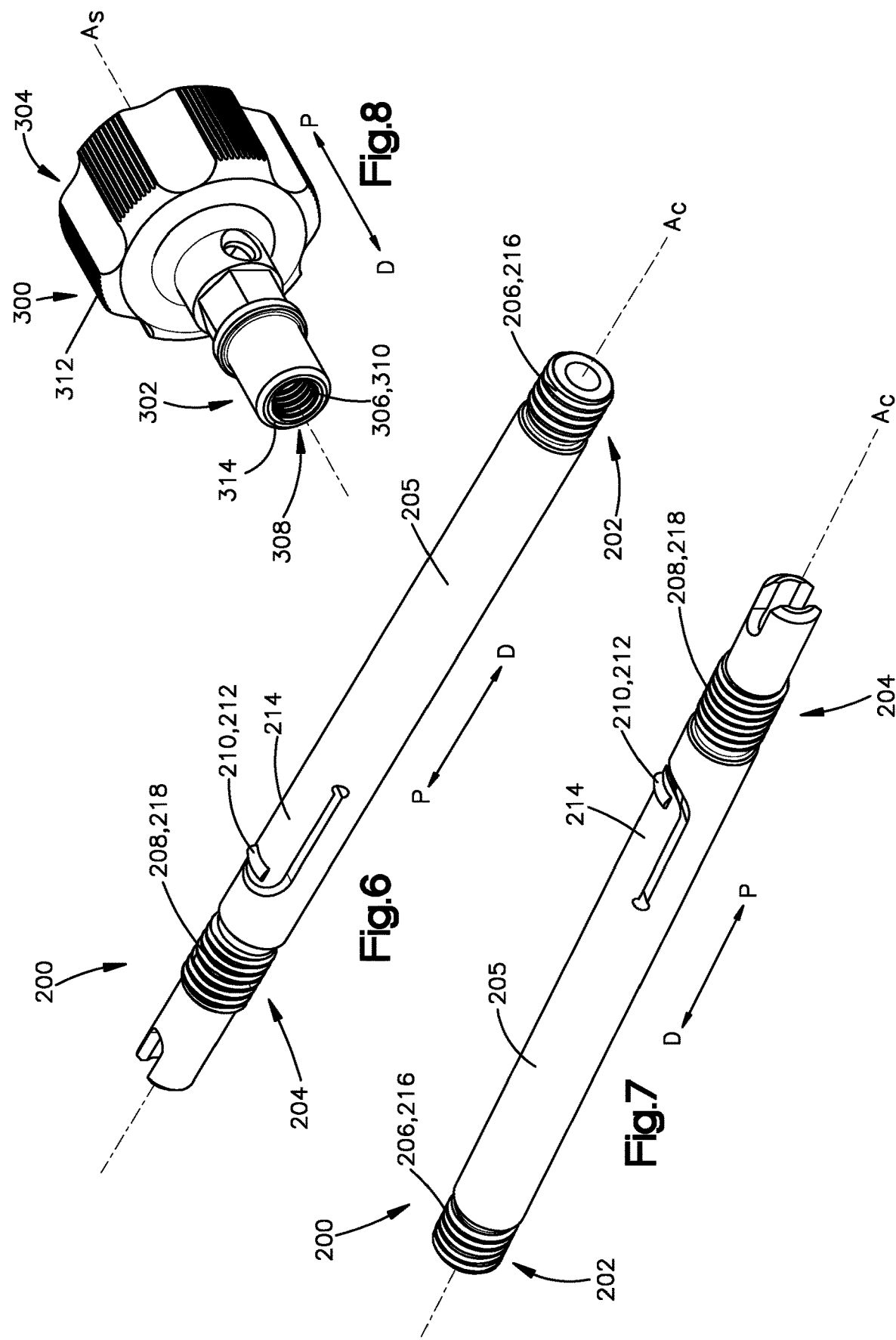

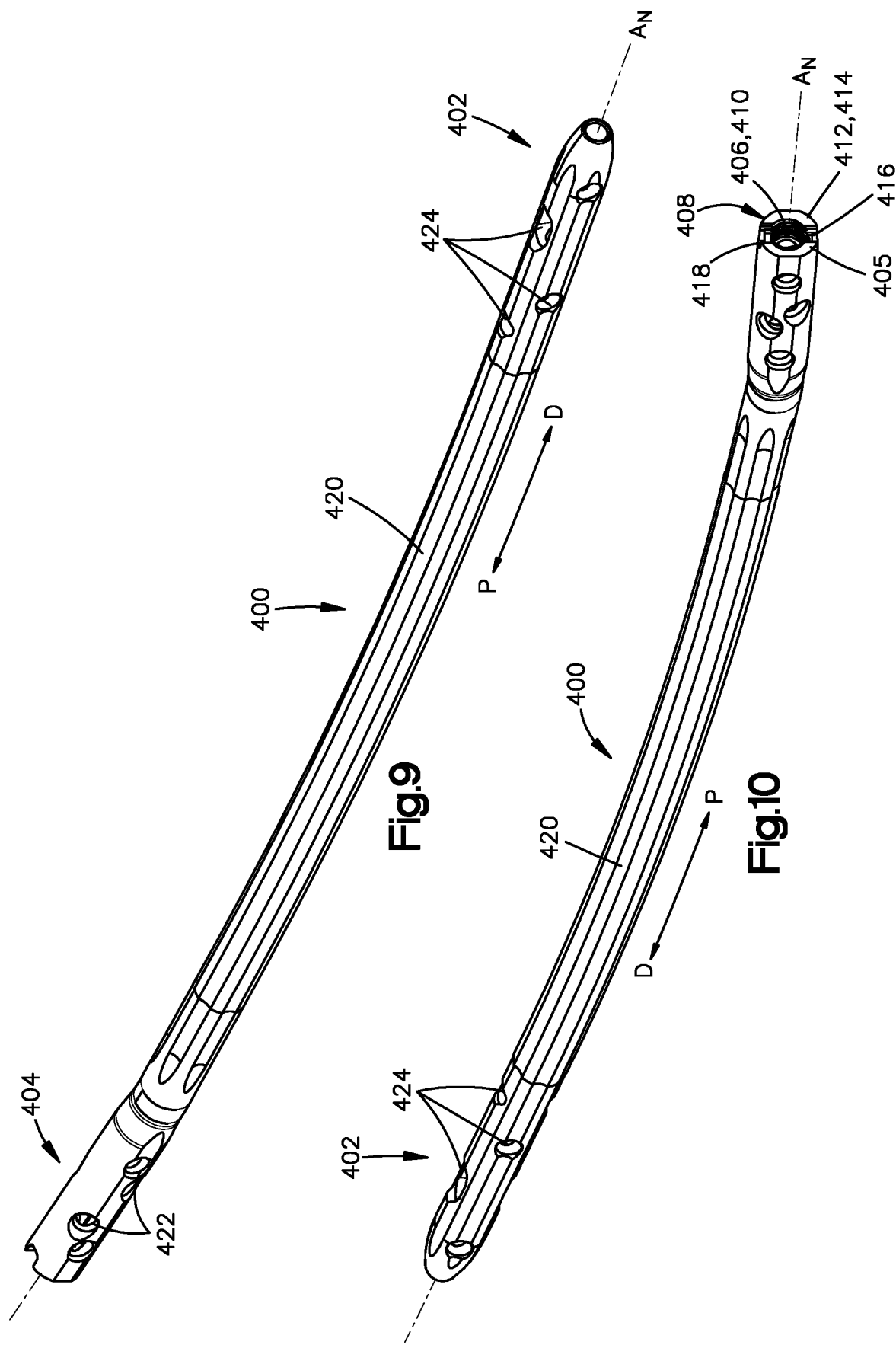

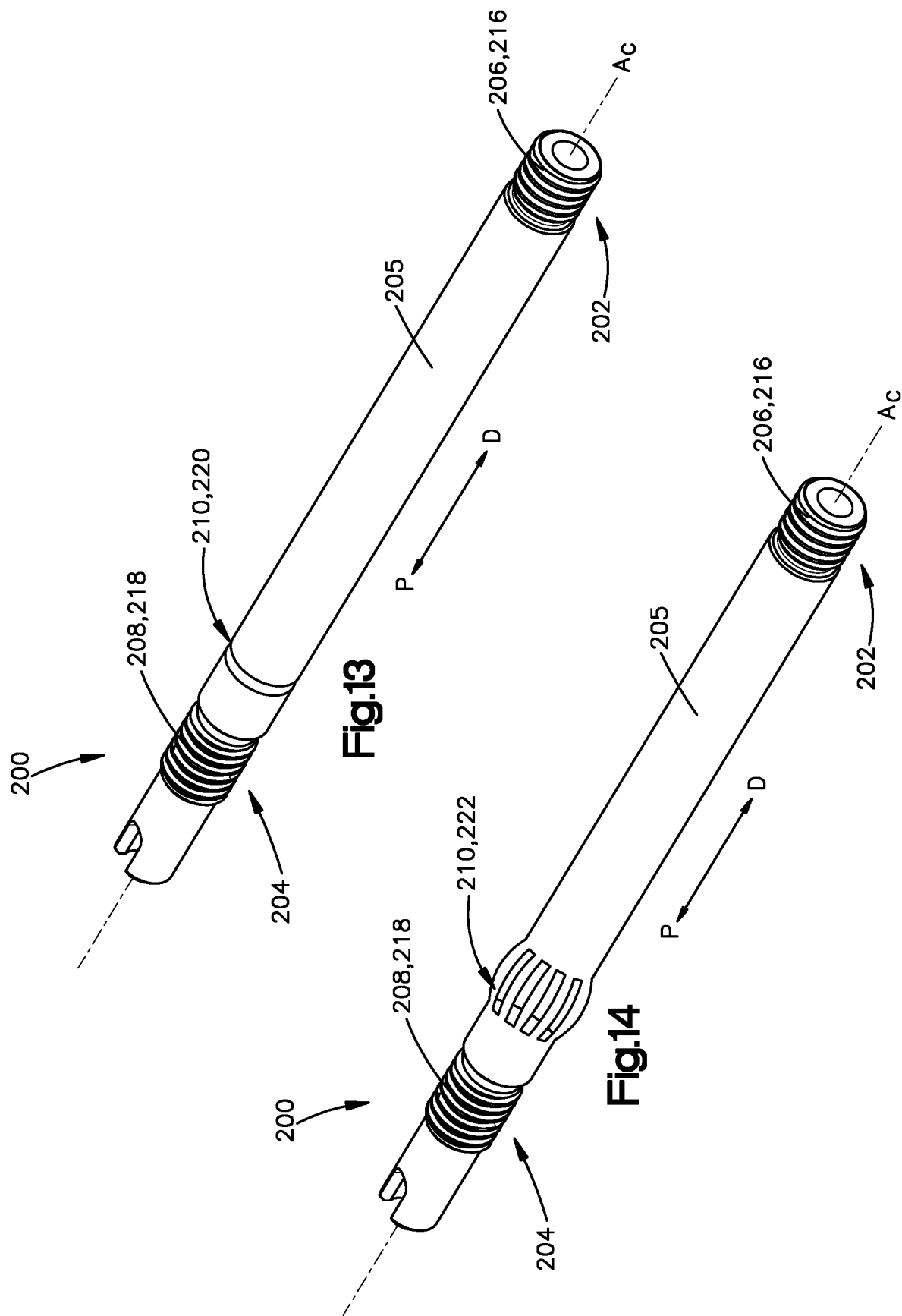

INTRAMEDULLARY NAIL INSERTION HANDLE

TECHNICAL FIELD

The present disclosure relates to systems, assemblies, and methods for the insertion and fixation of a nail into an intramedullary canal of a bone.

BACKGROUND

Intramedullary nails have long been used to treat fractures in long bones of the body such as fractures in femurs, tibias, and humeri. To treat such fractures, the intramedullary nail is inserted into a medullary canal of the long bone such that the nail extends spans across one or more fractures in the long bone to fragments of the long bone that are separated by the one or more fractures. Bone anchors are then inserted through the bone and into the intramedullary nail at opposing sides of the fracture, thereby fixing the intramedullary nail to the bone. The intramedullary nail can remain in the medullary canal at least until the fracture is fused.

SUMMARY

In an example embodiment, an intramedullary nail insertion system comprises a handle, a coupler, and a securement member. The handle has a body that includes a distal body end, and a proximal body end that is spaced from the distal body end along a proximal direction. The proximal body end defines a proximal body opening, and the distal body end defines a distal body opening. Further, the handle defines an aperture that extends through the body from the distal body opening to the proximal body opening. The coupler is sized to be at least partially received into the aperture. Further, the coupler includes a distal coupler end, and a proximal coupler end that is spaced from the distal coupler end. The distal coupler end includes a first fastener configured to fasten to an intramedullary nail, and the proximal coupler end includes a second fastener. The securement member has a third fastener configured to fasten to the second fastener of the coupler so as to capture the body between the securement member and the intramedullary nail when the proximal coupler end is received into the aperture and the first fastener of the coupler is fastened to the intramedullary nail.

In another example embodiment, an intramedullary nail insertion system comprises a handle and a coupler. The handle has a body that includes a distal body end, and a proximal body end that is spaced from the distal body end along a proximal direction along a body longitudinal axis. The proximal body end defines a proximal body opening, and the distal body end defines a distal body opening. The handle defines an aperture that extends through the body from the distal body opening to the proximal body opening. The distal body end is configured to interlock with an intramedullary nail so as to prevent rotation of the handle relative to the intramedullary nail about the body longitudinal axis. The coupler is sized to be at least partially received into the aperture. The coupler includes a distal coupler end, and a proximal coupler end that is spaced from the distal coupler end. The distal coupler end includes a first fastener configured to fasten to an intramedullary nail. The proximal coupler end is sized to be received in the proximal direction through the distal body opening in the distal body end and into the aperture.

In yet another example embodiment, a method for coupling a handle to an intramedullary nail comprises a step of fastening a distal end of a coupler to a proximal end of the intramedullary nail such that the coupler extends from the proximal end of the intramedullary nail to a proximal end of the coupler in a proximal direction. The method further comprises a step of receiving the proximal end of the coupler in the proximal direction through a distal opening in a distal end of a body of the handle such that the coupler extends into an aperture of the body that extends from the distal end of the body through a proximal end of the body. The method yet further comprises a step of fastening a securement member to the proximal end of the coupler so as to capture the body of the handle between the securement member and the intramedullary nail.

BRIEF DESCRIPTION OF THE DRAWINGS

The following description of the illustrative embodiments may be better understood when read in conjunction with the appended drawings. It is understood that potential embodiments of the disclosed systems and methods are not limited to those depicted.

FIG. 1 shows a perspective view of a subassembly according to one embodiment having a coupler fixed to an intramedullary nail;

FIG. 2 shows a perspective view of a subassembly according to one embodiment having a handle coupled to the subassembly of FIG. 1;

FIG. 3 shows a perspective view of an assembly according to one embodiment having a securement member coupled to the subassembly of FIG. 2;

FIG. 6 shows a perspective distal-end view of a coupler according to one embodiment;

FIG. 7 shows a perspective proximal-end view the coupler of FIG. 6;

FIG. 8 shows a perspective distal-end view of a securement member according to one embodiment;

FIG. 9 shows a perspective proximal-end view of an intramedullary nail according to one embodiment;

FIG. 10 shows a perspective distal-end view of an intramedullary nail according to one embodiment;

FIG. 13 shows a perspective side view of a coupler according to an alternative embodiment; and FIG. 14 shows a perspective side view of a coupler according to yet another alternative embodiment.

DETAILED DESCRIPTION OF ILLUSTRATIVE EMBODIMENTS

Figure 5:
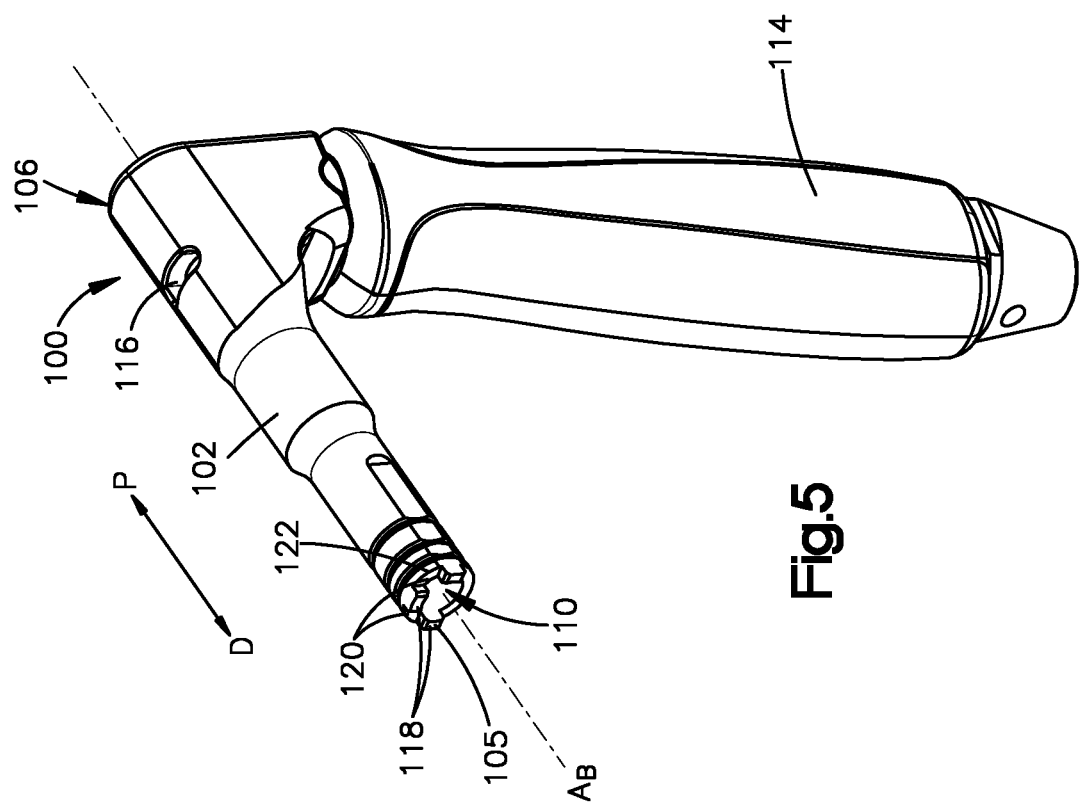
FIG. 5 shows a perspective proximal-end view of the handle of FIG. 4.

For insertion of an intramedullary nail, a handle is commonly affixed to the intramedullary nail that can be used to guide and force the intramedullary nail into an intramedullary canal of a bone. However, at least some conventional handles require more than two hands to hold the handle, the intramedullary nail, and other components used to affix the handle to the intramedullary nail. As a result, attaching the handle to the intramedullary nail can be cumbersome. Another problem with attaching a handle to an intramedullary nail is that the attachment between the handle and the intramedullary nail should be able to withstand the insertion forces needed to insert the intramedullary nail into the intramedullary canal of a bone. For example, the attachment should be able to withstand a bending force applied at the joint between the handle and the intramedullary nail in a direction that is perpendicular to a central axis of the intramedullary nail. Therefore, there is a need for handles that can be securely fastened to intramedullary nails using less cumbersome procedures, such as two-handed procedures, and methods of fastening such handles to intramedullary nails.

Referring briefly to FIGS. 1-3, assembly steps are shown for an intramedullary nail insertion system that includes a handle 100, a coupler 200, and a securement member 300. The system can further include an intramedullary nail 400, or the intramedullary nail 400 can be distributed separately from the system. It will be understood that the individual components of the system can be distributed individually, and therefore, embodiments of the disclosure are not limited solely to an assembly comprising all of the above-mentioned components.

The system can be assembled using a two-hand procedure as follows. In a first step (FIG. 1), the coupler 200 is fastened to the intramedullary nail 400 to form a first subassembly 10. While being fastened, the coupler 200 can be held with a first of two hands, and the intramedullary nail 400 can be held with a second of two hands. In a second step (FIG. 2), the handle 100 is coupled to the first subassembly 10 by receiving the coupler 200 into the handle 100 to form a second subassembly 20. The handle 100 can be held with a first of two hands, and the first assembly 10 can be held with a second of two hands at, for example, the intramedullary nail 400. Further, the handle 100 and coupler 200 can engage one another in the second step (FIG. 2) so as to limit translation of the handle 100 relative to the coupler 200 along the body longitudinal axis $A_B$ until the securement member 300 is fastened to the coupler 200. In a third step (FIG. 3), the securement member 300 is fastened to the second subassembly 20 to form an assembly 30. The securement member 300 can be held with a first of two hands, and the second assembly 20 can be held with a second of two hands at, for example, the intramedullary nail 400 or a handgrip of the handle 100. It will be understood that the order of the steps of assembling the individual components of the system can vary from those described above, and the system can be assembled using a procedure other than the two-handed procedure above.

In general, and with reference to FIGS. 4-8, the handle 100 has a body 102 that includes a distal body end 104, and a proximal body end 106 that is spaced from the distal body end 104 along a proximal direction P. The body 102 can extend from the distal body end 104 to the proximal body end along a body longitudinal axis $A_B$. The body 102 can be elongate from the distal body end 104 to the proximal body end along the body longitudinal axis $A_B$. The proximal body end 106 defines a proximal body opening 108, and the distal body end 104 defines a distal body opening 110. The handle 100 has an internal surface 111 that defines an aperture 112 (shown in FIG. 12) that extends through the body 102 from the distal body opening 110 to the proximal body opening 108.

The coupler 200 is sized to be received at least partially into the aperture 112. The coupler 200 includes a distal coupler end 202, and a proximal coupler end 204 that is spaced from the distal coupler end 202. The distal coupler end 202 includes a first fastener 206 configured to fasten to a proximal end of the intramedullary nail 400, and the proximal coupler end 204 includes a second fastener 208. In at least some embodiments, the proximal coupler end 204 is sized to be received in the proximal direction P through the distal body opening 110 of the handle 100.

The securement member 300 has a third fastener 306 configured to fasten to the second fastener 208 of the coupler 200 so as to capture the body 102 of the handle 100 between the securement member 300 and the intramedullary nail 400 when the proximal coupler end 204 is received through the distal body opening 110 of the handle 100 and the first fastener 206 of the coupler 200 is fastened to the intramedullary nail 400. Capturing the body 102 of the handle 100 between the securement member 300 and the intramedullary nail 400 prevents translation of the handle 100 along the proximal direction P and a distal direction D, opposite the proximal direction P, with respect to the intramedullary nail 400. As will be understood, the distal direction D can also be referred to as the insertion direction (i.e., the direction in which the intramedullary nail is inserted), and the proximal direction P can also be referred to as the trailing direction.

Figure 4:
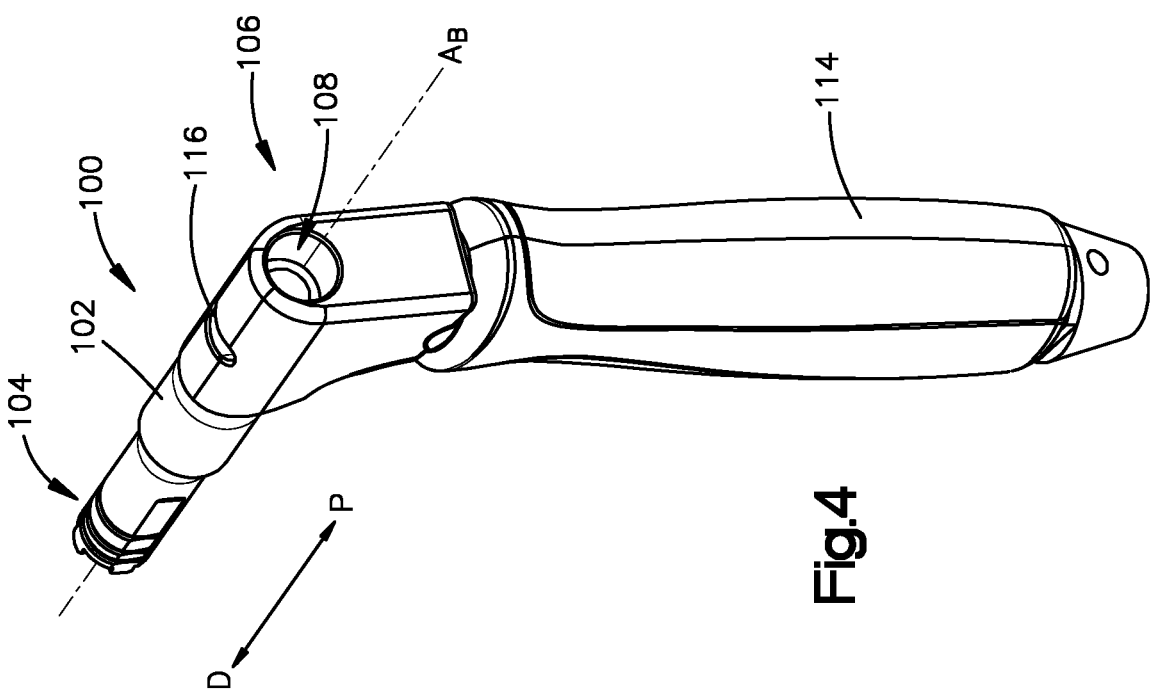
FIG. 4 shows a perspective distal-end view of a handle according to one embodiment.
Figure 11:
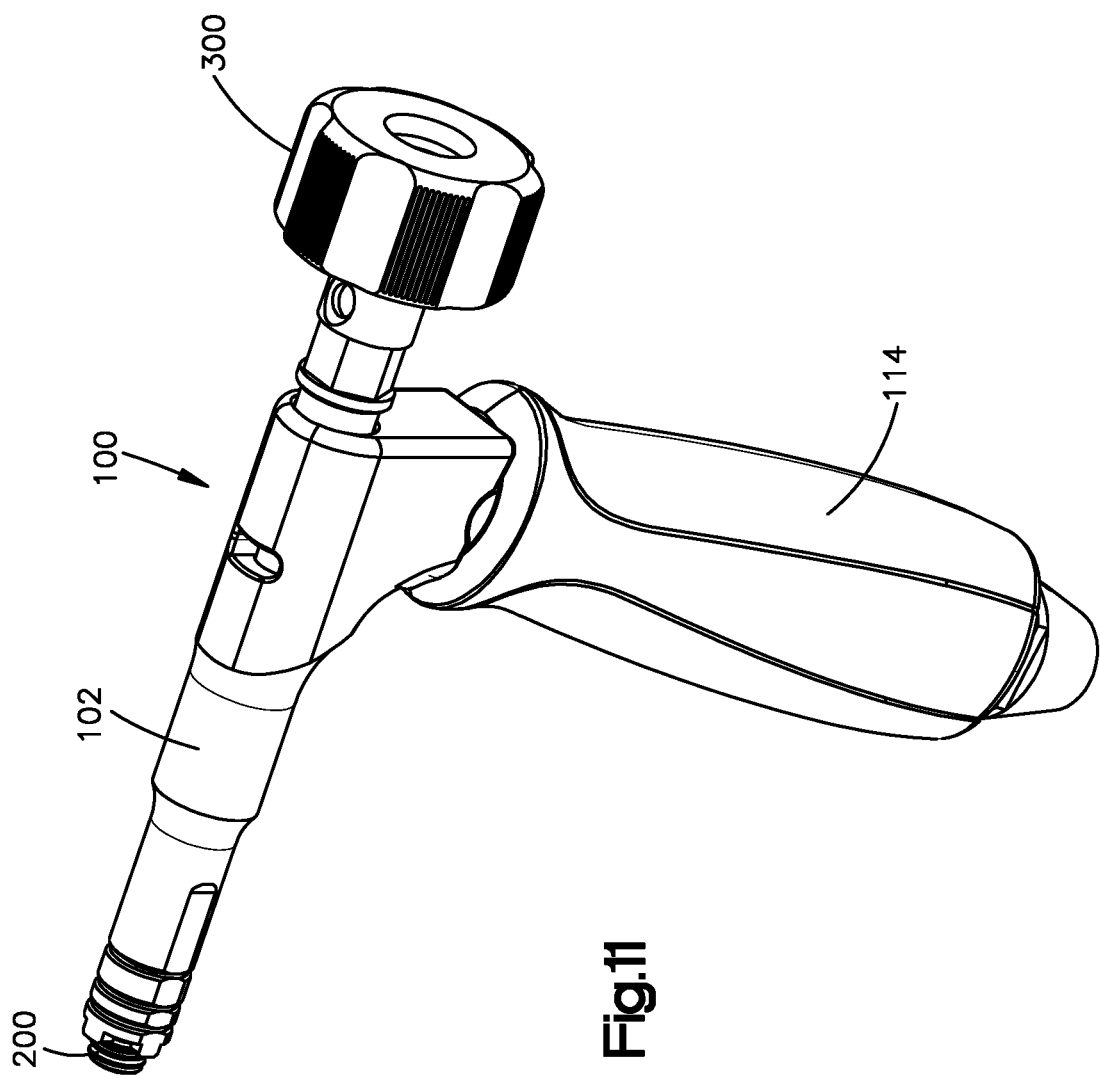
FIG. 11 shows a perspective proximal-end view of an assembly according to one embodiment that includes the handle of FIGS. 4 and 5, the coupler of FIGS. 6 and 7, and the securement member of FIG. 8.
Figure 12:
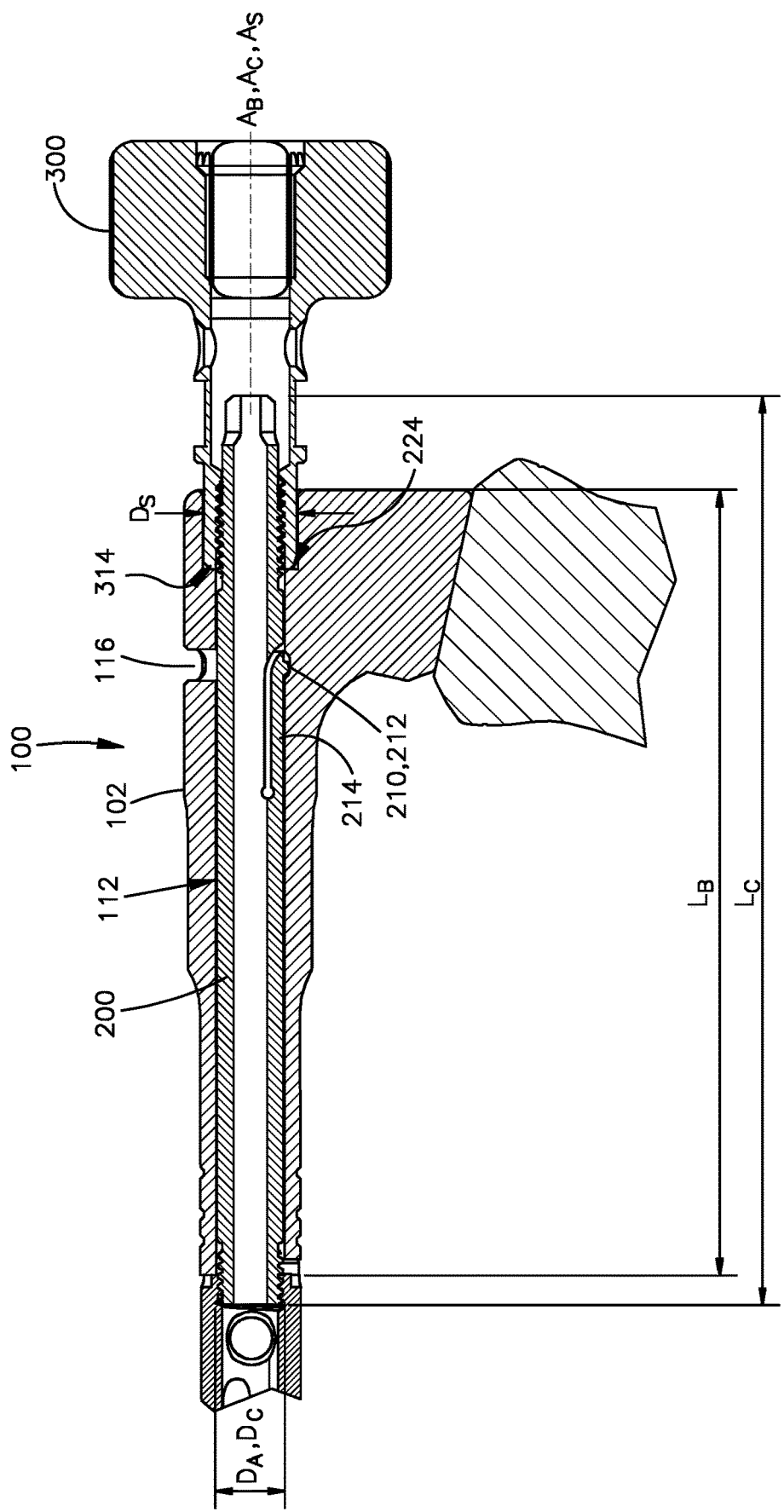
FIG. 12 shows a cross-sectional side view of the assembly of FIG. 11.

Referring more specifically to FIGS. 4, 5, and 12, the aperture 112 extends from the distal body opening 110 to the proximal body opening 108 along the body longitudinal axis $A_B$. The handle 100 can include a handgrip 114 that extends from the body 102 at an angle with respect to the body longitudinal axis $A_B$. The angle can be a non-zero angle. For example, the angle can be substantially perpendicular to the body longitudinal axis $A_B$. Further, the handgrip 114 can extend from the body 102 at the proximal body end 106 such that the handle 114 has a generally "L" shape. Note that, in alternative embodiments, the handgrip can be configured differently than that shown. For example, the handgrip can extend from locations other than the proximal body end 106, such as along a middle of the body 102 to form a "T" shape. As another example, the handgrip can be an outer surface of the body 102 of the handle 102 such that a hand grasping the handgrip wraps around the body 102. As another example, the handle 100 can include a plurality of handgrips such as two handgrips on opposed sides of the body longitudinal axis $A_B$.

The body 102 can include an engagement feature 116 that engages the coupler 200 so as to limit translation of the handle 100 relative to the coupler 200 along the body longitudinal axis $A_B$ when the coupler 200 is received in the handle 100 and before the securement member 300 is fastened to the coupler 200. In some embodiments, the engagement feature 116 can define a retention opening or recess in the body 102 that is configured to receive a protrusion (e.g., 212 of FIG. 6) of the coupler 200. In other embodiments (not shown), the engagement feature 116 can define a protrusion that is configured to be received in a retention opening or recess in the coupler 200. In yet other embodiments, the engagement feature 116 can be configured in any other suitable manner that limits translation of the handle 100 relative to the coupler 200 along the body longitudinal axis $A_B$ when the coupler 200 is received in the handle 100 and before the securement member 300 is fastened to the coupler 200.

The distal body end 104 can be configured to interlock with the intramedullary nail 400 so as to prevent rotation of the handle 100 about the body longitudinal axis $A_B$ relative to the intramedullary nail 400. For example, the distal body end 104 can include a fourth fastener 116 that fastens to a proximal end of the intramedullary nail 400. In one embodiment, the fourth fastener 116 can comprise at least one of a protrusion 118 and a recess 120 that is configured to engage a corresponding recess or protrusion of the intramedullary nail 400. For example, the fourth fastener 116 can comprise at least one protrusion 118, such a plurality of protrusions or teeth. Each protrusion can be configured to engage at least one corresponding recess in the intramedullary nail 400. Each of the at least one protrusion 118 can extend from a distal end surface 105 of the distal body end 104 towards the proximal body end 106. The fourth fastener 116 can define at least one recess 120, such as a plurality of recesses, that extends into the distal end surface 105 towards the proximal body end 106 to a floor 122 of the recess 120. Each of the at least one recess 120 can be configured to receive a corresponding protrusion of the intramedullary nail 400. Further, in embodiments having a plurality of protrusions 118, each of the at least one recess 120 can extend between a pair of the protrusions 118. Thus, in such embodiments, the protrusions 118 and recesses 120 can alternate around the distal body opening 110.

Turning to FIGS. 6 and 7, the coupler 200 extends from the distal coupler end 202 to the proximal coupler end 204 along a coupler longitudinal axis $A_C$. The coupler 200 can define a shaft or a tube. The coupler has an outer surface 205 that extends between the distal coupler end 202 and the proximal coupler end 204. For example, the outer surface 205 can extend from the distal coupler end 202 to the proximal coupler end 204. The outer surface 205 is generally circular in a plane that is perpendicular to the coupler longitudinal axis $A_C$. However, in alternative embodiments, at least a portion of the outer surface 205 between the distal and proximal coupler ends 202 and 204, up to an entirety of the outer surface 205, can have another other suitable shape, such as a square, triangle, etc.

The coupler 200 can include an engagement feature 210 that engages the body 102 of the handle 100 so as to limit translation of the coupler 200 relative to the body 102 along the coupler longitudinal axis $A_C$ when the coupler 200 is received in the handle 100 and before the securement member 300 is fastened to the coupler 200. In some embodiments, the engagement feature 210 can include at least one protrusion 212. As shown in FIG. 12, the at least one protrusion 212 configured to be received in the retention opening or recess 116 of the handle 100. Further, in some such embodiments, the engagement feature 210 can include a biasing element that includes the protrusion 212. The biasing element can include a spring arm 214 that includes the protrusion 212. The spring arm 214 can be configured to be resiliently biased away from the coupler longitudinal axis $A_C$. Thus, the spring arm 214 can be biased such that the spring arm 214 deflects towards the coupler longitudinal axis $C_A$ to a deflected position when a biasing force is applied to an outer surface thereof, and springs away from the coupler longitudinal axis $C_A$ to an undeflected position when the biasing force is removed.

In other embodiments such as shown in FIG. 13, the engagement feature 210 can define a retention opening or recess 220 in the coupler 200 that is configured to receive a protrusion of the handle 100. The retention opening or recess 220 can be an annular recess the extends into the outer surface 205 around the coupler longitudinal axis $A_C$, where the protrusion of the handle 100 can rotate around the annular recess 220 when the protrusion of the handle 100 is received in the annular recess 220. In yet other embodiments such as shown in FIG. 14, the coupler 200 can include a plurality of spring arms (not shown) that are biased outwardly away from the coupler longitudinal axis $A_C$ such that the spring arms form a friction fit with the inner surface of the body 102 of the handle 100. In such embodiments, the engagement feature 116 of the handle 100 can include the inner surface of the body 102. In yet further embodiments, the engagement feature 210 can be configured in any other suitable manner that limits translation of the handle 100 relative to the coupler 200 along the coupler longitudinal axis $A_C$ when the coupler 200 is received in the handle 100 and before the securement member 300 is fastened to the coupler 200. For example, the outer surface 205 of coupler 200 can be sized to form a friction fit with an inner surface of the body 102 of the handle 100.

Referring back to FIGS. 6 and 7, the first fastener 206 includes an outer surface sized to be received in the intramedullary nail 400. The first fastener can include male threading 216 configured to engage corresponding female threading of the intramedullary nail 400. The second fastener 208 includes an outer surface sized to be received in the third fastener 306 of the securement member 300. In this embodiment, the second 208 fastener includes male threading 218 configured to engage female threading of the securement member 300. In alternative embodiments, the second fastener 208 can include another suitable fastener, such as a fastener other than the threading 218.

The coupler 200 can be irreversible such that only the first fastener 206 is configured to fasten to the intramedullary nail 400, and only the second fastener 208 is configured to fasten to the securement member 300. Alternatively, the coupler 200 can be reversible such that the first fastener 206 and the second fastener 208 can each be selectively fastened to the intramedullary nail 400, and the first fastener 206 and the second fastener 208 can each be selectively fastened to the securement member 300. In such reversible embodiments, the coupler 200 can be symmetrical such that a first half of the coupler 200 from the proximal coupler end 204 towards the distal coupler end 208 is a mirror image of a second half of the coupler 200 from the distal coupler end 208 towards the proximal coupler end 204. For example, the engagement feature 210 can be centrally positioned such that it can be used in either the non-reversed or reversed orientation. Alternatively, the coupler 200 can have a first engagement feature disposed on the first half of the coupler 200 and a second engagement feature disposed on the second half of the coupler 200 in a position that is a mirror image of the position of the first engagement feature.

Referring to FIG. 12, the aperture 112 of the handle 100 is sized to receive the proximal coupler end 204. The aperture 112 has a cross-section in a plane that is perpendicular to the body longitudinal axis $A_B$, the cross-section having an aperture cross-sectional dimension $D_A$ along a select direction in the plane. The aperture cross-sectional dimension $D_A$ can be measured from a first point on the internal surface 111 to a second point on the internal surface 111, the first and second points being on opposed sides of the body longitudinal axis $A_B$. The coupler 200 has a cross-section in a plane that is perpendicular to the body longitudinal axis $A_B$, the cross-section having a coupler cross-sectional dimension $D_C$ along the select direction. The coupler cross-sectional dimension $D_C$ can be measured from a first point on the outer surface 205 of the coupler 200 to a second point on the outer surface 205, the first and second points being on opposed sides of the coupler longitudinal axis $A_C$. The aperture cross-sectional dimension $D_A$ is greater than the coupler cross-sectional dimension $D_C$ such that at least a portion of the coupler 200 is receivable in the aperture 112 of the handle 100. The aperture 112 can have a cross-sectional shape in a plane that is perpendicular to the body longitudinal axis $A_B$, where the shape conforms to a cross-sectional shape of the coupler 200 in a plane that is perpendicular to the coupler longitudinal axis $A_C$.

The body 102 of the handle 100 has a body length $L_B$ from the distal body opening 110 to the proximal body opening 108 along the body longitudinal axis $A_B$. The coupler 200 has a coupler length $L_C$ from the distal coupler end 202 to the proximal coupler end 204 along the coupler longitudinal axis $A_C$. The coupler length $L_C$ can be greater than the body length $L_B$ such that, when the coupler 200 is received in the aperture 112 of the handle 100, the proximal coupler end 204 extends out of the body 102 of the handle 100 along the proximal direction P, and the distal coupler end 202 extends out of the body 102 along the distal direction D. In alternative embodiments, the coupler length $L_C$ can be less than or equal to the body length $L_B$ such that, when the coupler 200 is received in the aperture 112 of the handle 100, the distal coupler end 202 extends from the body 102 of the handle 100 along the distal direction D, but the proximal coupler end 204 does not extend from the body 102 along the proximal direction P.

Turning now to FIG. 8, the securement member 300 can define a knob configured to be gripped by a user's hand to fasten the securement member 300 to the coupler 200. The securement member 300 has a distal securement-member end 302, and a proximal securement-member end 304 spaced from the distal securement-member end 302 along the proximal direction P. The proximal securement-member end 304 can include a handgrip 312, although embodiments of the disclosure are not so limited. The handgrip 312 can be gripped by a user's hand to fasten the securement member 300 to the coupler 200. The distal securement-member end 302 includes the third fastener 306. In some embodiments, the third fastener 306 can define an opening or recess 308 that extends into the distal securement-member end 302 along a securement-member longitudinal axis Cs, the opening or recess 308 sized to receive the second fastener 208. Further, in some embodiments, the third fastener 306 can include female threading 310 in the opening or recess 308, the female threading 310 configured to engage the male threading 218 of the second fastener 208. In alternative embodiments, the second and third fasteners 208 and 306 can be fasteners other than threading.

Referring to FIGS. 8 and 12, the securement member 300 can include a stop or a shoulder 314 configured to abut the handle 100 when securement member 300 is fastened to the coupler 200 so as to prevent the handle 100 from moving in the proximal direction P relative to the securement member 300. The stop or shoulder 314 has a stop cross-sectional dimension $D_S$ in a plane that is perpendicular to the securement-member longitudinal axis $A_S$. The stop cross-sectional dimension $D_S$ is measured from a first point on the stop or shoulder 314 to a second point on the stop or shoulder 314, the first and second points being on opposed sides of the securement-member longitudinal axis $A_S$. Further, the stop cross-sectional dimension $D_S$ is greater than the aperture cross-sectional dimension $D_A$ such that the stop or shoulder 314 is prevented from translating into the aperture 112 of the handle 100. Similarly, the handle 100 can include a stop or shoulder 124 configured to abut the securement member 300 when securement member 300 is fastened to the coupler 200 so as to prevent the handle 100 from moving in the proximal direction P relative to the securement member 300. The stop or shoulder 124 can abut the stop or shoulder 314.

Referring to FIGS. 9 and 10, an intramedullary nail 400 is shown according to one embodiment. It will be understood that intramedullary nail 400 is but one example, and that other intramedullary nails can be used with the system described herein. The intramedullary nail 400 has a distal or insertion end 402, and a proximal end 404 offset from the distal end 402 along the proximal direction P. The distal and proximal ends 402 and 404 can be spaced from one another along a central nail axis $A_N$ that can be straight as shown or bent. Further, the intramedullary nail 400 has an outer surface 420 that extends between the distal and proximal ends 402 and 404, such as from the distal end 402 to the proximal end 404. The proximal end 404 includes a fastener 406 that is configured to receive the fastener 206 of the coupler 200. For example, the fastener 406 can define a recess or opening 408 that is configured to receive the distal coupler end 202. The fastener 406 can include female threading 410 that engages male threading 216 of the distal coupler end 202.

The proximal end 404 can also include a fastener 412 that is configured to engage the fourth fastener 116 of the handle 100 so as to rotatably fix the handle 100 and intramedullary nail 400 relative to one another with respect to rotation about the body longitudinal axis $A_B$. In one embodiment, the fastener 412 can comprise at least one of a protrusion 414 and a recess 416 that is configured to engage a corresponding one of a recess 120 and a protrusion 118 of the handle 100. For example, the fastener 412 can comprise at least one protrusion 414, such a plurality of protrusions or teeth. Each protrusion 414 can be configured to engage at least one corresponding recess 120 in the handle 100. Each of the at least one protrusion 414 can extend from a proximal end surface 405 of the intramedullary nail 400 towards the distal end 402 of the nail. The fastener 414 can define at least one recess 416, such as a plurality of recesses, that extends into the proximal end surface 405 towards the distal body end 402 to a floor 418 of the recess 418. Each of the at least one recess 418 can be configured to receive a corresponding protrusion 118 of the handle 100. Further, in embodiments having a plurality of protrusions 414, each of the at least one recess 416 can extend between a pair of the protrusions 414. Thus, in such embodiments, the protrusions 414 and recesses 416 can alternate around the opening 408.

The intramedullary nail further defines a set of one or more proximal apertures 422 that extend through the outer surface 420 at the proximal end 404, and a set of one or more distal apertures 424 that extend through the outer surface 420 at the distal end 402. The set of one or more proximal apertures 422 are positioned to be disposed on a first side of a fracture in a bone that defines the intramedullary canal, and the set of one or more distal apertures 424 are positioned to be disposed on a second side of the fracture in the bone. Each proximal aperture 422 and each distal aperture 424 is configured to receive a bone anchor such that the bone anchor fixedly attaches the intramedullary nail 400 to the bone.

Referring back to FIGS. 1-3, a method for coupling the handle 100 to the intramedullary nail 400 comprises a step (e.g., FIG. 1) of fastening the distal coupler end 202 to the proximal end of the intramedullary nail 400 such that the coupler 200 extends from the proximal end of the intramedullary nail 400 to the proximal coupler end 204 in the proximal direction P. In at least some embodiments, the step of fastening the distal coupler end 202 can comprise engaging male threading 216 of the coupler 200 with female threading of the intramedullary nail 400. Engaging male threading 216 with female threading of the intramedullary nail 400 can provide for a secure attachment capable of withstanding the insertion forces needed to insert the intramedullary nail 400 into an intramedullary canal of a bone, such as a bending force applied at the joint between the coupler 200 and the intramedullary nail 400 in a direction that is perpendicular to a coupler central axis $A_C$ of the intramedullary nail 400.

The method further comprises a step (e.g., FIG. 2) of receiving the proximal coupler end 204 in the proximal direction P through the distal opening 110 in the distal body end 104 of the handle 100 such that the coupler 200 extends into the aperture 112 of the body 102 that extends from the distal body end 104 through the proximal body end 106. In at least some embodiments, the receiving step can comprise engaging an engagement feature 116 of the body 102 of the handle 100 with an engagement feature 210 of the coupler 200 so as to translationally fix the handle 100 to the coupler 200 with respect to movement along the proximal direction P and the distal direction D. For example, the engagement feature 116 of the body 102 can define a retention opening in the body 102, the engagement feature 210 of the coupler 200 can define a protrusion 212, and the receiving step can comprise engaging the protrusion 212 with the opening 116. Further, in some embodiments, the engagement feature 210 of the coupler 200 can include a spring arm 214 having the protrusion 212, and the receiving step can comprise applying a biasing force to the spring arm 214 to deflect the spring arm 214 inwards towards the coupler longitudinal axis of $A_C$ as the coupler 200 is received in the body 102 of the handle 100 until the biasing force is removed and the spring arm 214 springs away from the coupler longitudinal axis $A_C$ to engage the protrusion 212 with the opening 116.

The receiving step can additionally or alternatively comprise interlocking the distal body end 104 of the handle 100 with the intramedullary nail 400 such that the handle 100 and the intramedullary nail 400 are rotationally fixed relative to one another about the body longitudinal axis $A_B$ that extends from the proximal body end 106 to the distal body end 104. For example, the receiving step can comprise interlocking at least one protrusion 118 of the distal body end 104 with a corresponding recess in the intramedullary nail 400.

The method yet further comprises a step (e.g., FIG. 3) of fastening the securement member 300 to the proximal coupler end 204 so as to capture the body 102 of the handle 100 between the securement member 300 and the intramedullary nail 400. The step of fastening the securement member 300 fixes a position of the handle 100 so as to prevent the handle 100 from translating along the proximal direction P and the distal direction D, opposite the proximal direction P, with respect to the intramedullary nail 400. The step of fastening the securement member 300 can also comprise engaging female threading 310 of the securement member 300 with male threading 218 of the coupler 200.

While certain example embodiments have been described, these embodiments have been presented by way of example only and are not intended to limit the scope of the inventions disclosed herein. Thus, nothing in the foregoing description is intended to imply that any particular feature, characteristic, step, module, or block is necessary or indispensable. Indeed, the novel methods and systems described herein may be embodied in a variety of other forms; furthermore, various omissions, substitutions, and changes in the form of the methods and systems described herein may be made without departing from the spirit of the inventions disclosed herein. The accompanying claims and their equivalents are intended to cover such forms or modifications as would fall within the scope and spirit of certain of the inventions disclosed herein.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

What is claimed:

1. An intramedullary nail insertion system, comprising:
a handle having a body that includes a distal body end, and a proximal body end that is spaced from the distal body end along a proximal direction, the proximal body end defining a proximal body opening, the distal body end defining a distal body opening, and the handle defining an aperture that extends through the body from the distal body opening to the proximal body opening;
a coupler sized to be at least partially received into the aperture, the coupler including a distal coupler end, and a proximal coupler end that is spaced from the distal coupler end, the distal coupler end including a first fastener configured to fasten to an intramedullary nail, and the proximal coupler end including a second fastener; and
a securement member having a third fastener configured to fasten to the second fastener of the coupler so as to capture the body between the securement member and the intramedullary nail when the proximal coupler end is received into the aperture and the first fastener of the coupler is fastened to the intramedullary nail;
wherein at least one of the body and the coupler includes an engagement feature that engages another of the body and the coupler so as to limit translation of the handle relative to the coupler along the proximal direction when the proximal coupler end is received through the distal body opening and before the securement member is fastened to the coupler.

2. The intramedullary nail insertion system of claim 1, wherein the proximal coupler end and the distal body opening each have a cross-sectional dimension in a plane perpendicular to the proximal direction, and the cross-sectional dimension of the distal body opening is greater than the cross-sectional dimension of the proximal coupler end such that the proximal coupler end is sized to be received in the proximal direction through the distal body opening and into the aperture.

3. The intramedullary nail insertion system of claim 1, wherein the handle is prevented from translating along the proximal direction and a distal direction, opposite the proximal direction, with respect to the intramedullary nail, when the body is captured between the securement member and the intramedullary nail.

4. The intramedullary nail insertion system of claim 1, wherein the handle includes a handgrip that extends from the body at a non-zero angle with respect to the proximal direction.

5. The intramedullary nail insertion system of claim 1, wherein the engagement feature defines a retention recess in the body that is configured to receive a protrusion of the coupler.

6. The intramedullary nail insertion system of claim 5, wherein the coupler has a spring arm that includes the protrusion, and the spring arm is configured to be resiliently biased away from a longitudinal axis of the coupler that extends from the distal coupler end to the proximal coupler end.

7. The intramedullary nail insertion system of claim 1, wherein the distal body end is configured to interlock with the intramedullary nail so as to prevent rotation of the handle relative to the intramedullary nail about a longitudinal axis of the intramedullary nail.

8. The intramedullary nail insertion system of claim 7, wherein the distal body end comprises at least one of a protrusion and recess that is configured to mate with a corresponding one of a protrusion and a recess of the intramedullary nail.

9. The intramedullary nail insertion system of claim 1, wherein the first fastener of the coupler includes male threading configured to engage female threading of the intramedullary nail.

10. The intramedullary nail insertion system of claim 1, wherein the securement member defines a knob configured to be gripped by a user's hand to fasten the securement member to the coupler.

11. An intramedullary nail insertion system, comprising:
a handle having a body that includes a distal body end, and a proximal body end that is spaced from the distal body end along a proximal direction along a body longitudinal axis, the proximal body end defining a proximal body opening, and the distal body end defining a distal body opening, the handle defining an aperture that extends through the body from the distal body opening to the proximal body opening, and the distal body end being configured to interlock with an intramedullary nail so as to prevent rotation of the handle relative to the intramedullary nail about the body longitudinal axis; and
a coupler sized to be at least partially received into the aperture, the coupler including a distal coupler end, and a proximal coupler end that is spaced from the distal coupler end, the distal coupler end including a first fastener configured to fasten to an intramedullary nail, and the proximal coupler end including a second fastener, the proximal coupler end being sized to be received in the proximal direction through the distal body opening in the distal body end and into the aperture such that the second fastener is configured to fasten to a securement member,
wherein at least one of the handle and the coupler includes an engagement feature that is configured to engage another of the handle and the coupler so as to limit translation of the coupler relative to the body along the body longitudinal axis when the coupler is received in the handle.

12. The intramedullary nail insertion system of claim 11, wherein the body is elongate along a body longitudinal axis that extends from the proximal body end to the distal body end.

13. The intramedullary nail insertion system of claim 11, wherein the proximal coupler end and the distal body opening each have a cross-sectional dimension in a plane perpendicular to the proximal direction, and the cross-sectional dimension of the distal body opening is greater than the cross-sectional dimension of the proximal coupler end such that the proximal coupler end is sized to be received in the proximal direction through the distal body opening and into the aperture.

14. The intramedullary nail insertion system of claim 11, wherein the handle includes a handgrip that extends from the body at a non-zero angle with respect to the proximal direction.

15. The intramedullary nail insertion system of claim 11, wherein the distal body end comprises at least one of a protrusion and recess that is configured to interlock with a corresponding one of a protrusion and a recess of the intramedullary nail.

16. The intramedullary nail insertion system of claim 11, wherein the first fastener of the coupler includes male threading configured to engage female threading of the intramedullary nail.

17. A method for coupling a handle to an intramedullary nail, the method comprising steps of:
fastening a distal end of a coupler to a proximal end of the intramedullary nail such that the coupler extends from the proximal end of the intramedullary nail to a proximal end of the coupler in a proximal direction;
receiving the proximal end of the coupler in the proximal direction through a distal opening in a distal end of a body of the handle such that the coupler extends into an aperture of the body that extends from the distal end of the body through a proximal end of the body; and
fastening a securement member to the proximal end of the coupler so as to capture the body of the handle between the securement member and the intramedullary nail;
wherein the receiving step comprises engaging an engagement feature of the body of the handle with an engagement feature of the coupler so as to prevent translation of the handle relative to the coupler along the proximal direction.

18. The method of claim 17, wherein the receiving step comprises interlocking the distal end of the body with the intramedullary nail such that the handle and the intramedullary nail are rotationally fixed relative to one another about a longitudinal axis of the body that extends from the proximal end of the body to a distal end of the body.

* * * * *